US010195019B2

(12) United States Patent
Sato

(10) Patent No.: US 10,195,019 B2
(45) Date of Patent: Feb. 5, 2019

(54) INTRAOCULAR LENS INSERTION APPARATUS

(71) Applicant: KOWA COMPANY, LTD., Nagoya-shi, Aichi (JP)

(72) Inventor: Takashi Sato, Nagoya (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 41 days.

(21) Appl. No.: 15/037,469

(22) PCT Filed: Nov. 19, 2014

(86) PCT No.: PCT/JP2014/080675
§ 371 (c)(1),
(2) Date: May 18, 2016

(87) PCT Pub. No.: WO2015/076308
PCT Pub. Date: May 28, 2015

(65) Prior Publication Data
US 2016/0278914 A1    Sep. 29, 2016

(30) Foreign Application Priority Data
Nov. 19, 2013  (JP) .................................. 2013-239061

(51) Int. Cl.
*A61F 2/16*    (2006.01)

(52) U.S. Cl.
CPC .......... *A61F 2/1675* (2013.01); *A61F 2/1678* (2013.01)

(58) Field of Classification Search
CPC .... A61F 2/1675; A61F 2/1678; A61F 2/1662; A61F 2/1664; A61F 2/1667; A61F 2/167; A61F 2/1672; A61M 5/427
See application file for complete search history.

(56) References Cited

U.S. PATENT DOCUMENTS 5,292,325 A * 3/1994 Gurmarnik ........... A61M 5/427
128/DIG. 26
2003/0212406 A1  11/2003 Kobayashi et al.
(Continued)

FOREIGN PATENT DOCUMENTS

EP    2072025 A1     6/2009
JP    2003-325569 A  11/2003
(Continued)

OTHER PUBLICATIONS

Extended European Search Report issued in corresponding European Patent Application No. 14864525.2, dated Jun. 23, 2017, in 6 pages.
(Continued)

*Primary Examiner* — Diane Yabut
(74) *Attorney, Agent, or Firm* — Knobbe, Martens, Olson & Bear, LLP

(57) ABSTRACT

An intraocular lens insertion apparatus includes an accommodating member integrally or independently formed on an apparatus body which is inserted into an eyeball, allowing arrangement of the intraocular lens in the apparatus body by accommodating the intraocular lens therein, and having a hole through which a needle of a syringe which supplies a lubricant to the intraocular lens passes. Further, the intraocular lens insertion apparatus includes a guide wall member formed on the accommodating member at a position adjacent to the hole, and being configured to guide the needle of the syringe to the hole.

17 Claims, 15 Drawing Sheets

(56) References Cited

U.S. PATENT DOCUMENTS

| | | | |
|---|---|---|---|
| 2004/0160575 A1 | 8/2004 | Ayton et al. | |
| 2004/0243141 A1 | 12/2004 | Brown et al. | |
| 2007/0168026 A1 | 7/2007 | Nagasaka | |
| 2009/0149812 A1* | 6/2009 | MacAulay | A61M 5/427 604/117 |
| 2010/0130985 A1 | 5/2010 | Tanaka | |
| 2013/0226193 A1 | 8/2013 | Kudo et al. | |
| 2014/0114323 A1 | 4/2014 | Kudo et al. | |

FOREIGN PATENT DOCUMENTS

| | | | |
|---|---|---|---|
| JP | 2004-351196 A | 12/2004 | |
| JP | 2007-185255 A | 7/2007 | |
| JP | 2011-255029 A | 12/2011 | |
| WO | WO 2012027516 A2 * | 3/2012 | A61F 2/167 |
| WO | WO 2012/086797 A1 | 6/2012 | |
| WO | WO 2013/137208 A1 | 9/2013 | |

OTHER PUBLICATIONS

Notification of Reasons for Refusal in connection with Japanese Patent Application No. 2015-549176 dated Jul. 17, 2018.f.
Decision of Refusal issued in corresponding Japanese Patent Application No. 2015-549176 dated Oct. 23, 2018.

* cited by examiner

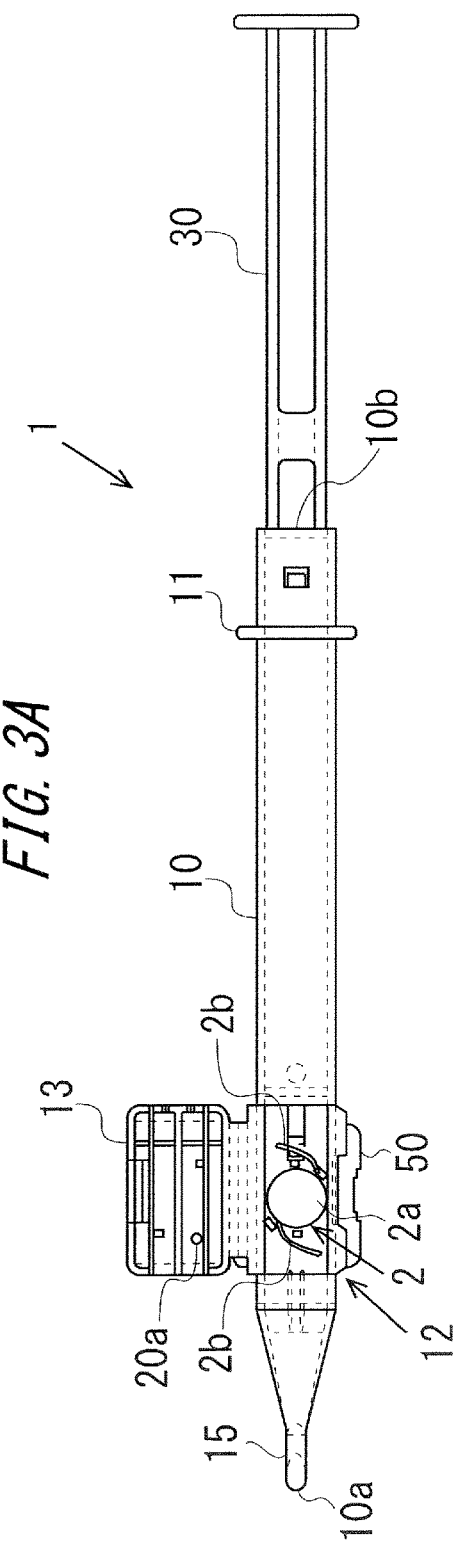
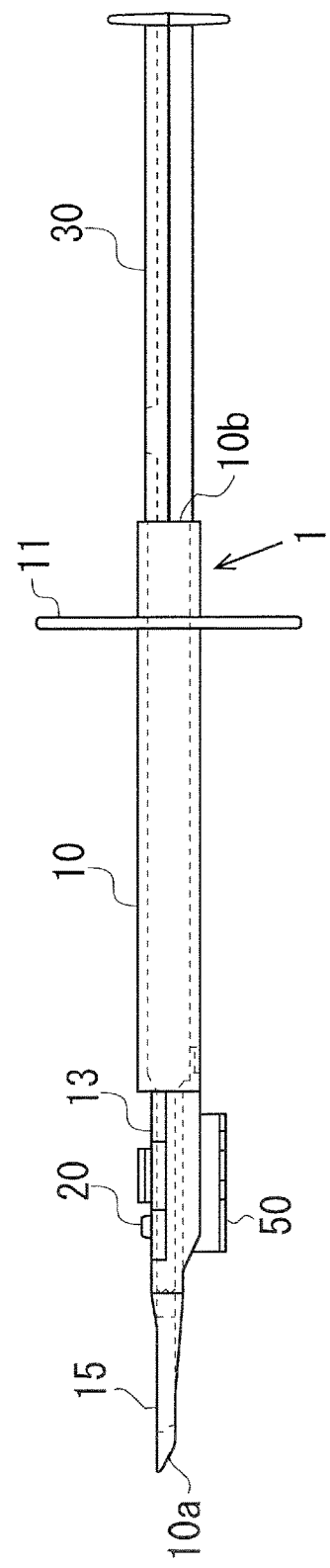

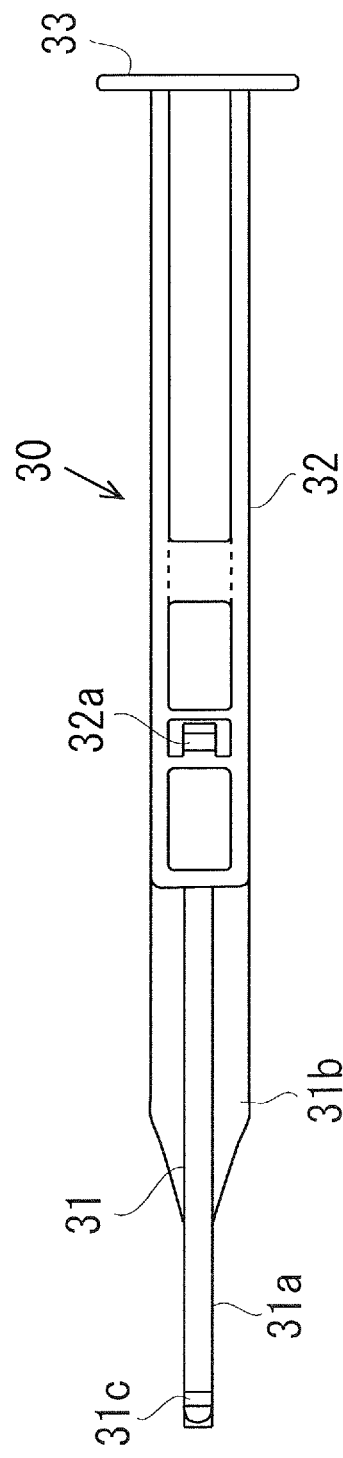
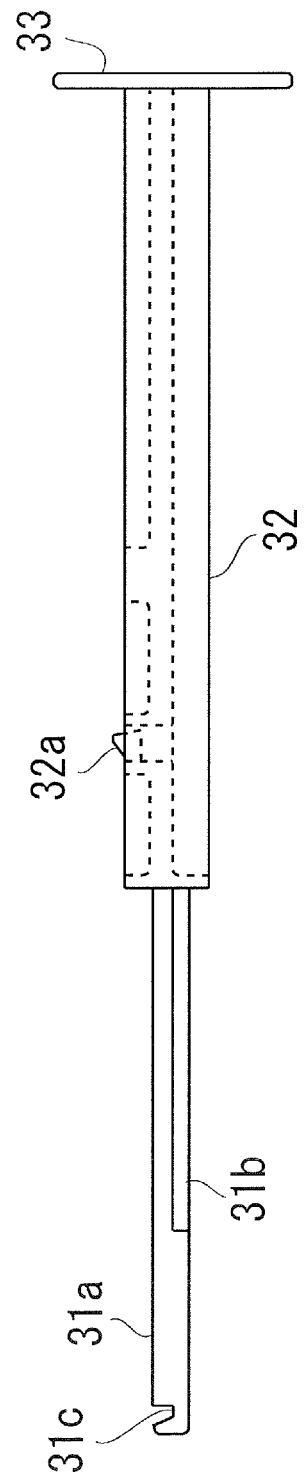
FIG. 7A
FIG. 7B

# INTRAOCULAR LENS INSERTION APPARATUS

CROSS-REFERENCE TO RELATED APPLICATIONS

This application is the U.S. National Phase under 35 U.S.C. § 371 of International Application PCT/JP2014/080675, filed Nov. 19, 2014, which claims priority to JP 2013-239061, filed Nov. 19, 2013 the entire contents of which are incorporated herein by reference.

FIELD

The embodiments discussed herein pertain to an intraocular lens insertion apparatus.

BACKGROUND

Intraocular lenses are widely used to be replaced with human opacity crystalline lenses in cataract treatments or normal human crystalline lenses for compensating the optical powers of the lenses. In intraocular lens insertion surgeries for the cataract treatments, a discission wound (cut) which is several millimeters in length is produced at the edge of the cornea, the human crystalline lens is crushed and removed by phacoemulsification and aspiration etc. and the intraocular lens is inserted and fixed in the eye, for example.

Recently, in inserting an intraocular lens into the inside of an eyeball through the incision, it is often the case that a so-called preload (or preset) type insertion apparatus is used where the intraocular lens is placed in an accommodating member in advance. A user inserts a distal end opening of an inserting sleeve member formed on a distal end member of an apparatus body into the inside of an eyeball through the above-mentioned incision, and also in a state where the intraocular lens is deformed into a compact shape in the inside of the apparatus body, the intraocular lens is pushed out by a rod-like plunger through the distal end opening of the inserting sleeve member so that the intraocular lens is released and inserted into the inside of the eyeball. With the use of such an insertion apparatus, an intraocular lens can be easily inserted into an eyeball by making use of an incision which is formed for taking out and removing a crystalline lens. Accordingly, an operation can be simplified and, at the same time, the occurrence of astigmatism and the occurrence of an infectious disease after the operation can be suppressed.

In inserting an intraocular lens into an eyeball using the above-mentioned insertion apparatus, with an aim to enable smooth movement of the intraocular lens in the inside of the insertion apparatus toward the distal end opening of the inserting sleeve member, there may be a case where viscoelastic material such as hyaluronic acid is injected into the inside of the insertion apparatus as a lubricant for the intraocular lens, and the viscoelastic material is interposed between the intraocular lens and an inner wall of the insertion apparatus. With such a configuration, friction resistance between the intraocular lens and the insertion apparatus is reduced thus enabling the smoother movement of the intraocular lens in the inside of the insertion apparatus. Further, in injecting the viscoelastic material into the inside of the insertion apparatus, a needle of a syringe is inserted into the inside of the insertion apparatus through a hole formed in the insertion apparatus, and the viscoelastic material is injected into particularly a place where the intraocular lens is accommodated in the inside of the insertion apparatus by the syringe.

CITATION LIST

Patent literature

[PTL 1] JP-A-2011-255029

SUMMARY

Technical Problem

In the conventional insertion apparatus, however, the hole through which the needle of the syringe is inserted is barely visible and hence, it is often the case that whether or not the needle of the syringe can be skillfully advanced into the inside of the insertion apparatus through the hole depends on experience and sense of touch of a user.

The technique of this disclosure has been made in view of the above-mentioned circumstances, and it is an object of this disclosure to realize an insertion apparatus which supports the injection of a lubricant into an accommodating member for an intraocular lens.

Solution to Problem

According to an embodiment, it is provided an intraocular lens insertion apparatus, including an accommodating member integrally or independently formed on an apparatus body which is inserted into an eyeball, allowing arrangement of the intraocular lens in the apparatus body by accommodating the intraocular lens therein, and having a hole through which a needle of a syringe which supplies a lubricant to the intraocular lens passes; and a guide wall member formed on the accommodating member at a position adjacent to the hole, and being configured to guide the needle of the syringe to the hole. With such a configuration, in injecting a lubricant for the intraocular lens into the accommodating member, a user can guide the needle of the syringe in which a lubricant is filled to the hole by the guide wall member while checking the hole.

Further, the guide wall member is configured so as to prevent the needle of the syringe from coming into contact with a lens body of the intraocular lens accommodated in the accommodating member in a state where the needle of the syringe which is made to pass through the hole is brought into contact with the guide wall.

Further, at least a part of the guide wall member is configured to surround the hole. A distance from the center of the hole to a predetermined portion of an inner wall of the guide wall member may be set shorter than a distance from the center of the hole to the other portion of the inner wall of the guide wall member. The guide wall member has an opening member which allows movement of the needle of the syringe within a range where the needle of the syringe which is made to pass through the hole is not brought into contact with a lens body of the intraocular lens accommodated in the accommodating member. An inclined member which connects an inner wall of the guide wall member and the hole may be formed on the guide wall member. Further, a stepped member may be formed on the guide wall member by setting a height of an inner wall side of the guide wall member in a thickness direction lower than a height of an outer wall of the guide wall member. With such a configuration, the user can more easily guide the needle of the syringe to the hole.

Further, the hole is formed on a distal end side of the apparatus body with respect to the intraocular lens accommodated in the accommodating member. With such a configuration, when a lubricant is injected from the needle of the syringe which is inserted into the hole, the lubricant can be injected toward a more distal end side of the insertion sleeve member with respect to the intraocular lens. Accordingly, in moving the intraocular lens toward the distal end of the inserting sleeve member, a lubricant can be supplied to the intraocular lens with more certainty.

In addition, an intraocular lens insertion apparatus may include: an accommodating member integrally or independently formed on an apparatus body which is inserted into an eyeball, allowing arrangement of the intraocular lens in the apparatus body by accommodating the intraocular lens therein, and having a hole through which a needle of a syringe which supplies a lubricant to the intraocular lens passes; and a guide wall member formed on the accommodating member at a position adjacent to the hole, and being configured to guide the needle of the syringe to the hole, wherein the intraocular lens is accommodated in the accommodating member before the insertion apparatus is placed on a market.

Advantageous Effects of Invention

According to the technique disclosed herein, it is possible to realize the insertion apparatus which can inject a lubricant into an insertion member of an intraocular lens more easily compared to the prior art.

BRIEF DESCRIPTION OF DRAWINGS

FIG. 3A and FIG. 3B are diagrams illustrating the schematic configuration of the intraocular lens insertion apparatus according to one embodiment;

FIG. 7A and FIG. 7B are diagrams illustrating the schematic configuration of a plunger according to one embodiment;

DESCRIPTION OF EMBODIMENTS

Hereinafter, an embodiment of the present invention is described with reference to drawings.

EXAMPLE

Figure 1:
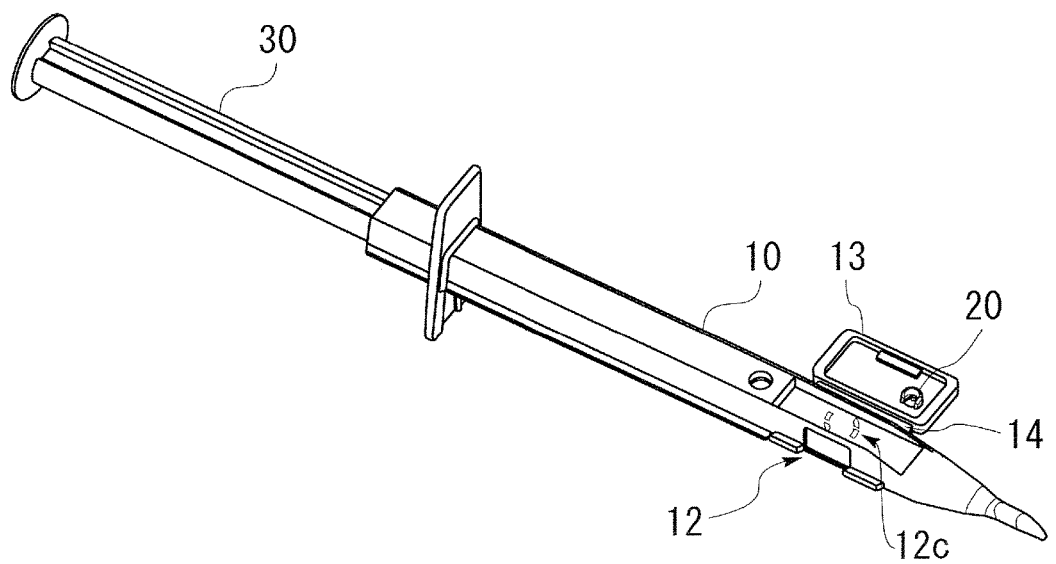
FIG. 1 is a diagram illustrating the schematic configuration of an intraocular lens insertion apparatus according to one embodiment.

FIG. 1 is a perspective diagram illustrating a whole intraocular lens insertion apparatus 1 of the present embodiment (hereinafter, also simply referred to as an insertion apparatus 1). The insertion apparatus 1 includes a nozzle body 10 which forms an apparatus body, a plunger 30 which forms a push member for pushing an intraocular lens, and a stage member 12 and a stage lid member 13 which form an accommodating member for accommodating an intraocular lens. The stage member 12 is integrally or independently formed on the nozzle body 10. The plunger 30 is inserted into the nozzle body 10. An intraocular lens 2 is set in the stage member 12. The stage member 12 is integrally formed with the stage lid member 13. FIG. 1 illustrates a state where the stage lid member 13 is opened. Further, FIG. 1 illustrates an upper surface of the stage lid member 13. An insertion member 20 for a needle of a syringe filled with a lubricant for the intraocular lens is formed on the stage lid member 13. Setting surface through-holes 12c for assembling a positioning member 50 for positioning the intraocular lens 2 are formed in the nozzle body 10. The detailed configuration of the positioning member 50 is described later. As can be understood from the description made hereinafter with reference to FIG. 3, FIG. 1 is a perspective diagram when the intraocular lens insertion apparatus 1 is viewed from below. Accordingly, the insertion member 20 is configured to project toward the outside of the stage lid member 13 when the stage lid member 13 is closed.

Figure 2:
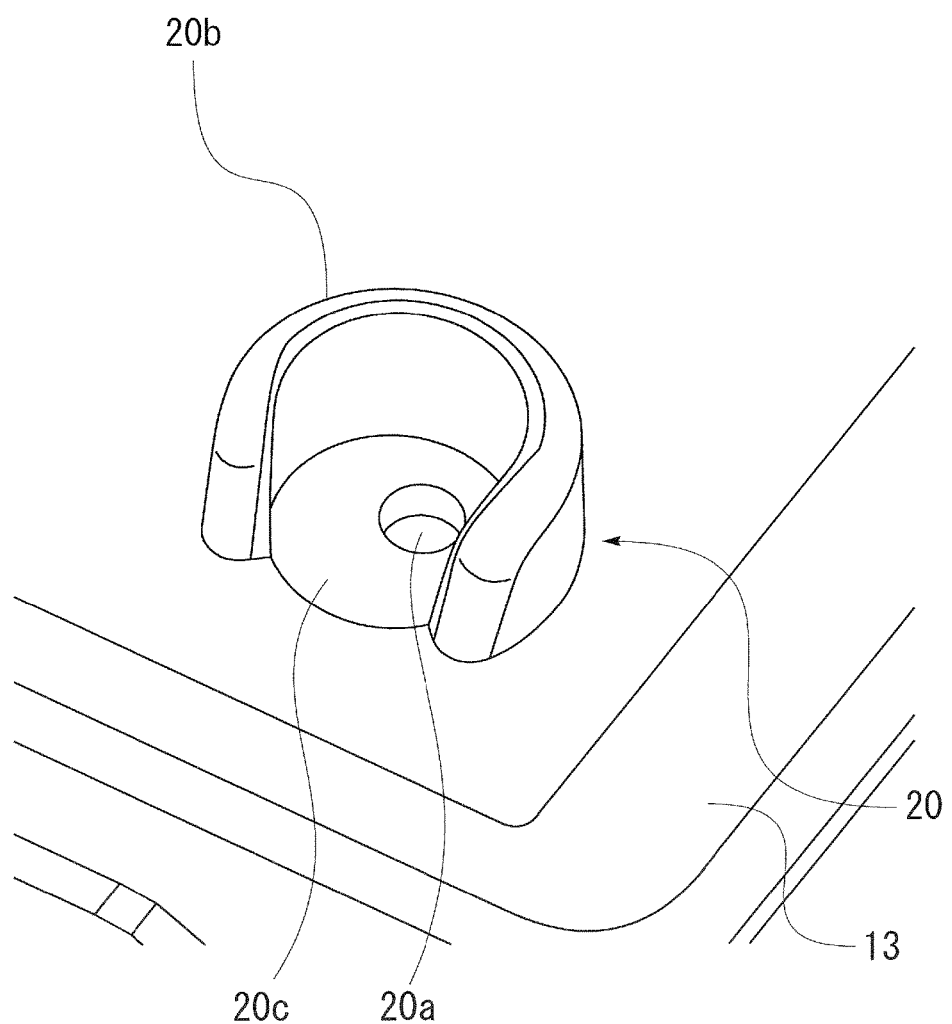
FIG. 2 is a diagram illustrating the schematic configuration of an insertion member for a needle of a syringe according to one embodiment.

FIG. 2 illustrates an enlarged diagram of the insertion member 20 for a needle of a syringe inserted. As illustrated in FIG. 2, the insertion member 20 has: a needle hole 20a which is a hole into which a needle of a syringe is inserted; and a guide wall member 20b which guides a distal end of the needle of the syringe into the needle hole 20a. As described later, the guide wall member 20b also has a function of restricting the movement, the inclination, the rotation and the like of a needle of a syringe after the needle is inserted into the needle hole 20a. Further, an inclined member 20c which extends downward toward the needle hole 20a is formed on the stage lid member 13 at a region surrounded by the guide wall member 20b. The intraocular lens 2 is placed and positioned on the stage member 12. When the positioning of the intraocular lens 2 with respect to the stage member 12 is completed, the stage lid member 13 is closed by rotating the stage lid member 13 about a connecting member 14 between the stage lid member 13 and the stage member 12.

Next, when the plunger 30 is pushed into a nozzle body 10 side, the plunger 30 is brought into contact with the intraocular lens 2 placed on the stage member 12. When the plunger 30 is further pushed into the nozzle body 10 side, the intraocular lens 2 is moved to a distal end member 10a of the nozzle body 10 from the stage member 12 through a nozzle member 15 connected with the stage member 12. Then, the intraocular lens 2 is pushed out through an opening of the distal end member 10a.

FIG. 3A and FIG. 3B illustrate the schematic configuration of the insertion apparatus 1 of the present embodiment. FIG. 3A is a plan diagram of the insertion apparatus 1 when the stage lid member 13 is opened, and FIG. 3B is a side diagram of the insertion apparatus 1 when the stage lid member 13 is closed. The nozzle body 10 of the insertion apparatus 1 is formed as a tube with an approximately rectangular cross section, an end member of the nozzle body 10 on one side is largely opened (hereinafter, the largely-opened side is referred to as a rear end member 10b), and a nozzle member 15 which forms a tapered insertion cylindrical member and the distal end member 10a are formed on an end member of the nozzle body 10 on the other side. As illustrated in FIG. 3B, the distal end member 10a has an obliquely formed opening. The plunger 30 is inserted into the nozzle body 10 and is movable in an extensible and retractable manner.

In the description made hereinafter, the direction extending toward the distal end member 10a from the rear end member 10b of the nozzle body 10 is assumed as the frontward direction, the direction opposite to the frontward direction is assumed as the rearward direction, the direction toward a viewer's side with respect to a paper surface on which FIG. 3A is drawn is assumed as the upward direction, the direction opposite to the upward direction is assumed as the downward direction, the direction toward a viewer's side with respect to a paper surface on which FIG. 3B is drawn is assumed as the leftward direction, and the direction opposite to the leftward direction is assumed as the rightward direction. In this case, an upper side corresponds to a front side along an optical axis of a lens body 2a described later, a lower side corresponds to a rear side along the optical axis of the lens body 2a, a front side corresponds to a front side in the pushing direction of the plunger 30, and a rear side corresponds to a rear side in the pushing direction of the plunger 30.

A hold member 11 which projects in a plate shape and on which a user hooks his fingers when he pushes the plunger 30 toward the distal end side of the nozzle body 10 is integrally formed on the nozzle body 10 in the vicinity of the rear end member 10b of the nozzle body 10. The stage member 12 on which the intraocular lens 2 is to be set is formed on a member of the nozzle body 10 behind the nozzle member 15. The stage member 12 is configured such that an upper side of the nozzle body 10 is opened by opening the stage lid member 13. The positioning member 50 is mounted on the stage member 12 from below the nozzle body 10. With the use of the positioning member 50, the intraocular lens 2 is stably held in the stage member 12 even before the insertion apparatus 1 is used (during transportation).

That is, in the insertion apparatus 1, at the time of manufacturing the insertion apparatus 1, the intraocular lens 2 is set on the stage member 12 such that a front side along an optical axis is directed upward in a state where the stage lid member 13 is opened and the positioning member 50 is mounted on the stage member 12. Then, the insertion apparatus 1 is shipped after the stage lid member 13 is closed, and the insertion apparatus 1 is sold. Then, at the time of using the insertion apparatus 1, a user inserts a needle of a syringe filled with a lubricant for an intraocular lens into the inside of the stage member 12 through the needle hole 20a of the insertion member 20 and injects the lubricant. Then, the user removes the positioning member 50 while holding the stage lid member 13 in a closed state and, thereafter, pushes the plunger 30 toward the distal end side of the nozzle body 10. Due to such an operation, the intraocular lens 2 is pushed by the plunger 30 so as to move the intraocular lens 2 to the nozzle member 15, and the intraocular lens 2 is released into the inside of an eyeball from the distal end member 10a. In the insertion apparatus 1, the nozzle body 10, the plunger 30, and the positioning member 50 are formed using a resin such as polypropylene. Polypropylene has been proven as a material used for medical apparatuses. In addition, polypropylene is reliable in chemical resistance etc.

Figure 4A:
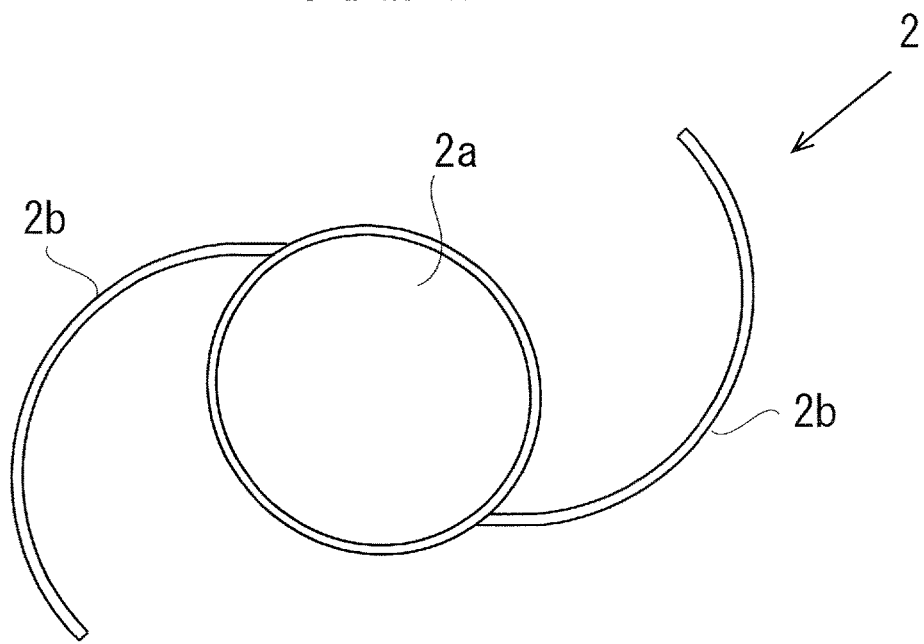
FIG. 4A and FIG. 4B are diagrams illustrating the schematic configuration of an intraocular lens according to one embodiment.
Figure 4B:
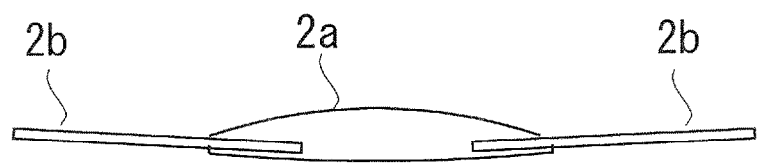

FIG. 4A and FIG. 4B are diagrams illustrating the schematic configuration of the intraocular lens 2. FIG. 4A is a plan diagram, and FIG. 4B is a side diagram. The intraocular lens 2 is a so-called three-piece type intraocular lens. The intraocular lens 2 is formed of the lens body 2a having a predetermined refractivity, and two whisker-like support members 2b, 2b which are connected to the lens body 2a and are provided for holding the lens body 2a in the inside of an eyeball. Both the lens body 2a and the support members 2b are formed using a flexible resin material. As a matter of course, the present invention is also applicable to an insertion apparatus for inserting a so-called one-piece-type intraocular lens where a support member and an optical member are formed into one member by molding. In the inside of the insertion apparatus 1 of the present embodiment, the intraocular lens 2 is set such that one of two support members 2b, 2b is arranged on a rear side of the lens body 2a, and the other of two support members 2b, 2b is arranged on a front side of the lens body 2a.

Figure 5:
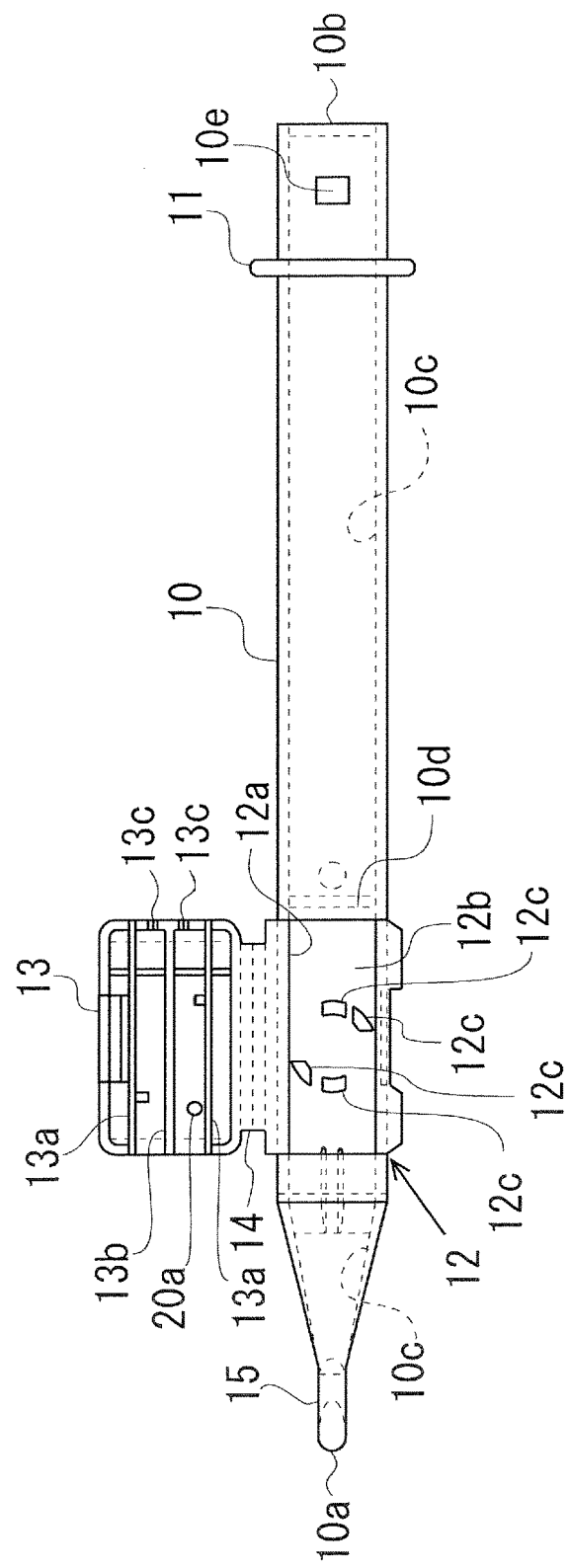
FIG. 5 is a diagram illustrating the schematic configuration of a nozzle body according to one embodiment.

FIG. 5 is a plan diagram of the nozzle body 10. As described previously, in the nozzle body 10, the intraocular lens 2 is set on the stage member 12. In such a state, the intraocular lens 2 is pushed by the plunger 30, and is released from the distal end member 10a. Here, a through-hole 10c whose cross-sectional shape changes corresponding to a change in a profile of the nozzle body 10 is formed in the inside of the nozzle body 10. In the release of the intraocular lens 2, the intraocular lens 2 is deformed corresponding to a change in a cross-sectional shape of the through-hole 10c formed in the inside of the nozzle body 10, and is released after being deformed into a shape which facilitates the entrance of the intraocular lens 2 into the incision formed in an eyeball of a patient.

The distal end member 10a has an obliquely cut shape such that an upper region of the nozzle member 15 extends more toward a front side than a lower region of the nozzle member 15. The obliquely cut shape of the distal end member 10a may be formed by obliquely cutting the distal end member 10a so as to have a straight line shape as viewed from a lateral direction or may be formed by obliquely cutting the distal end member 10a so as to have an outwardly bulging shape or a curved surface shape.

A stage groove 12a having a width slightly larger than a diameter of the lens body 2a of the intraocular lens 2 is formed on the stage member 12. A size of the stage groove 12a in the longitudinal direction is set larger than a total size of the intraocular lens 2 including the support members 2b, 2b extending from both sides of the intraocular lens 2. A setting surface 12b is formed of a bottom surface of the stage groove 12a. The position of the setting surface 12b in a vertical direction is set higher than the height position of a bottom surface of the through-hole 10c formed in the nozzle body 10, and the setting surface 12b and the bottom surface of the through-hole 10c are connected to each other by a bottom member inclined surface 10d.

The stage member 12 and the stage lid member 13 are integrally formed with each other. A size of the stage lid member 13 in the longitudinal direction is set substantially equal to a size of the stage member 12 in the longitudinal direction. The stage lid member 13 is connected to the stage member 12 by a thin-plate-like connecting member 14 which is formed in an extending manner toward the stage lid member 13 side from a side surface of the stage member 12. The connecting member 14 is formed in a bendable manner at a center portion thereof, and the stage lid member 13 overlaps with the stage member 12 from above by bending the connecting member 14 so that the stage lid member 13 is closed.

In the stage lid member 13, ribs 13a and a rib 13b for reinforcing the stage lid member 13 and for stabilizing the position of the intraocular lens 2 are formed on a surface of the stage lid member 13 which faces the setting surface 12b in an opposed manner in a lid closed state. Guide projections 13c are formed on the stage lid member 13 as an upper guide for the plunger 30. Further, the needle hole 20a is formed in the stage lid member 13 as an insertion hole for injecting a hyaluronic acid into the stage member 12 using a syringe before an operation of inserting the intraocular lens 2 into the inside of an eyeball is performed. The needle hole 20a is a hole which connects the outside of the stage member 12 and the intraocular lens 2 accommodated in the stage member 12 to each other when the stage lid member 13 is closed. A user inserts a needle of a syringe through the needle hole 20a before the insertion operation of the intraocular lens 2 is performed, and supplies a hyaluronic acid to the necessary position in the inside of the stage member 12.

Figure 6A:
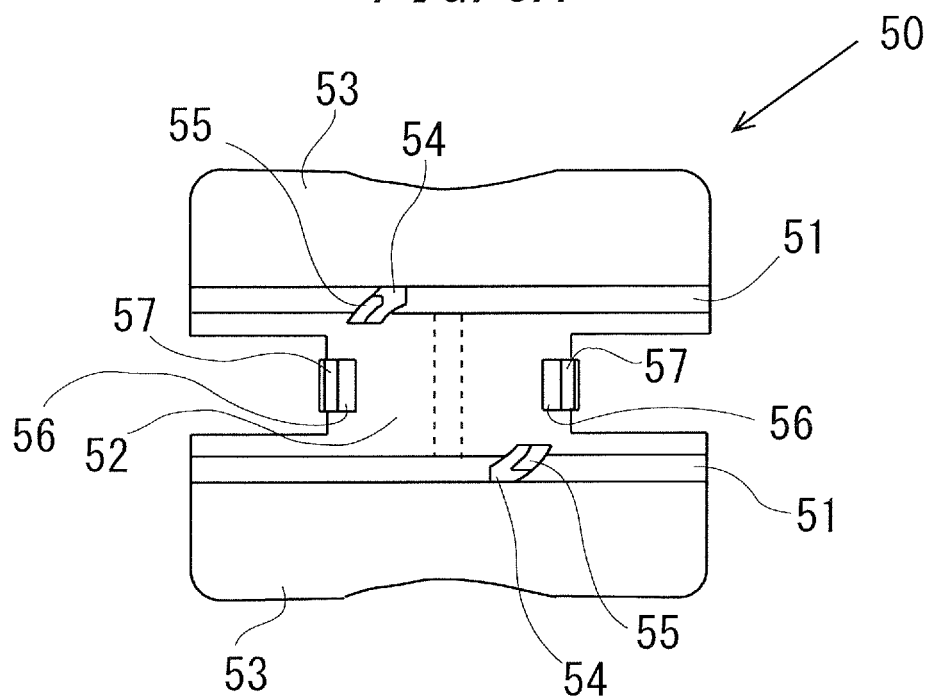
FIG. 6A and FIG. 6B are diagrams illustrating the schematic configuration of a positioning member according to one embodiment.
Figure 6B:
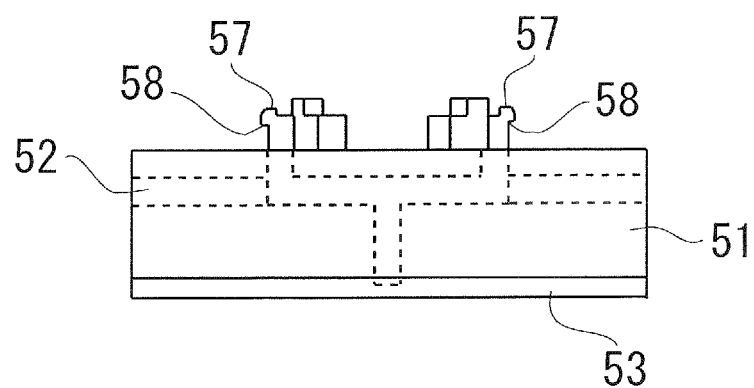

The positioning member 50 is detachably mounted on a lower side of the setting surface 12b of the stage member 12. FIG. 6A and FIG. 6B illustrate schematic configuration of the positioning member 50. FIG. 6A is a plan diagram of the positioning member 50, and FIG. 6B is a left side diagram of the positioning member 50. The positioning member 50 is formed as a body separate from the nozzle body 10, and is configured such that a pair of side wall members 51, 51 is connected to each other by a connecting member 52. Holding members 53, 53 which extend and expand outwardly are formed on lower ends of the side wall members 51 respectively.

A pair of first placing members 54, 54 which has an arcuate shape as viewed from above and projects upward is formed on upper end members of the respective side wall members 51, 51. First positioning members 55, 55 are formed on outer peripheral sides of upper end surfaces of the first placing members 54, 54 in a projecting manner. A distance between inner arcuate peripheral sides of the first positioning members 55, 55 is set slightly larger than a diameter size of the lens body 2a of the intraocular lens 2.

A pair of second placing members 56, 56 which has a rectangular shape as viewed from above and projects upward is formed on both ends of the connecting member in a longitudinal direction. A height of upper surfaces of the second placing members 56, 56 is set substantially equal to a height of the upper surfaces of the first placing members 54, 54. Second positioning members 57, 57 which project further upward are formed on outer portions of the upper surfaces of the second placing members 56, 56 such that the second positioning members 57, 57 extend over the whole regions of the second placing members 56, 56 in the lateral direction. A distance between inner sides of the second positioning members 57, 57 is set slightly larger than the diameter size of the lens body 2a of the intraocular lens 2. In addition, engaging pawls 58, 58 which project slightly in the longitudinal direction respectively are formed on upper end members of the second placing members 56, 56 respectively over the whole region of the upper end members in the lateral direction.

The above-mentioned positioning member 50 is assembled to the nozzle body 10 from below the setting surface 12b of the nozzle body 10. The setting surface through-holes 12c which penetrate the setting surface 12b in a thickness direction are formed in the setting surface 12b of the nozzle body 10. Profiles of the setting surface through-holes 12c have a shape slightly larger than and substantially similar to a shape of the first placing members 54, 54 and a shape of the second placing members 56, 56 of the positioning member 50 as viewed from above. When the positioning member 50 is mounted on the nozzle body 10, the first placing members 54, 54 and the second placing members 56, 56 are inserted into the setting surface through-holes 12c from below the setting surface 12b, and project upward from the setting surface 12b.

At this stage of operation, the engaging pawls 58, 58 respectively formed on the second positioning members 57, 57 project from the setting surface 12b through the setting surface through-holes 12c, and are engaged with the upper surface of the setting surface 12b. With such a configuration, the positioning member 50 is assembled to the nozzle body 10 from below, and the first placing members 54, 54 and the second placing members 56, 56 are fixed to the setting surface 12b in a state where the first placing members 54, 54 and the second placing members 56, 56 project from the setting surface 12b. Then, in setting the intraocular lens 2 on the setting surface 12b, a bottom surface of an outer peripheral portion of the lens body 2a is placed on the upper surfaces of the first placing members 54, 54 and the upper surfaces of the second placing members 56, 56. The position of the lens body 2a in a horizontal direction (a direction horizontal to the setting surface 12b) is restricted by the first positioning members 55, 55 and the second positioning members 57, 57.

FIG. 7 illustrates the schematic configuration of the plunger 30. A longitudinal length of the plunger 30 is set slightly larger than that of the nozzle body 10. The plunger 30 is formed of: an operating member 31 which is disposed on a distal end side and basically has a circular columnar shape; and an insertion member 32 which is disposed on a rear end side and basically has a rectangular rod shape. The operating member 31 is configured to include: a circular columnar member 31a having a circular columnar shape; and thin-plate-shaped flat members 31b expanding in the lateral direction from the circular columnar member 31a.

A notch member 31c is formed on a distal end portion of the operating member 31. As can be understood from FIG. 7A and FIG. 7B, the notch member 31c is formed on the operating member 31 in a groove shape such that notch member 31c opens upward and penetrates the operating member 31 in a lateral direction. As can be understood from FIG. 7B, a groove wall disposed on a distal end side of the notch member 31c is formed of an inclined surface which extends upward as the inclined surface extends toward the distal end side of the operating member 31.

On the other hand, the insertion member 32 has an approximately H-shaped cross section as a whole, and a size of the insertion member 32 in the lateral direction and a size of the insertion member 32 in the vertical direction are set slightly smaller than those of the through-hole 10*c* formed in the nozzle body 10. A disc-shaped pushing plate member 33 which expands in the vertical direction as well as in the lateral direction is formed on a rear end of the insertion member 32.

A pawl member 32*a* which projects toward an upper side of the insertion member 32 and is vertically movable due to elasticity of a raw material of the plunger 30 is formed on a portion of the insertion member 32 on a distal end side from the center in the longitudinal direction. When the plunger 30 is inserted into the nozzle body 10, an engaging hole 10*e* illustrated in FIG. 3 which is formed in the upper surface of the nozzle body 10 in a thickness direction and the pawl member 32*a* are engaged with each other. With such engagement, the relative position between the nozzle body 10 and the plunger 30 in an initial state is determined. The position where the pawl member 32*a* is formed and the position where the engaging hole 10*e* is formed are set such that, in an engaging state, a distal end of the operating member 31 is positioned behind the lens body 2*a* of the intraocular lens 2 set on the stage member 12, and the support members 2*b* on a rear side of the lens body 2*a* can be supported by the notch member 31*c* from below.

Before the intraocular lens 2 is accommodated in the insertion apparatus 1 having the above-mentioned configuration, the plunger 30 is arranged at an initial position in a state where the plunger 30 is inserted into the nozzle body 10. As described previously, the positioning member 50 is mounted on the nozzle body 10 from below the setting surface 12*b*. With such a configuration, the first placing members 54, 54 and the second placing members 56, 56 of the positioning member 50 are held in a projecting manner from the setting surface 12*b*.

Next, the lens body 2*a* of the intraocular lens 2 is placed and positioned on the upper surfaces of the first placing members 54, 54 and the upper surfaces of the second placing members 56, 56 in a state where the support members 2*b*, 2*b* are directed in the longitudinal direction of the nozzle body 10. In such a state, the support member 2*b* on a rear side of the intraocular lens 2 is supported by a bottom surface of the notch member 31*c* of the plunger 30.

Figure 8A:
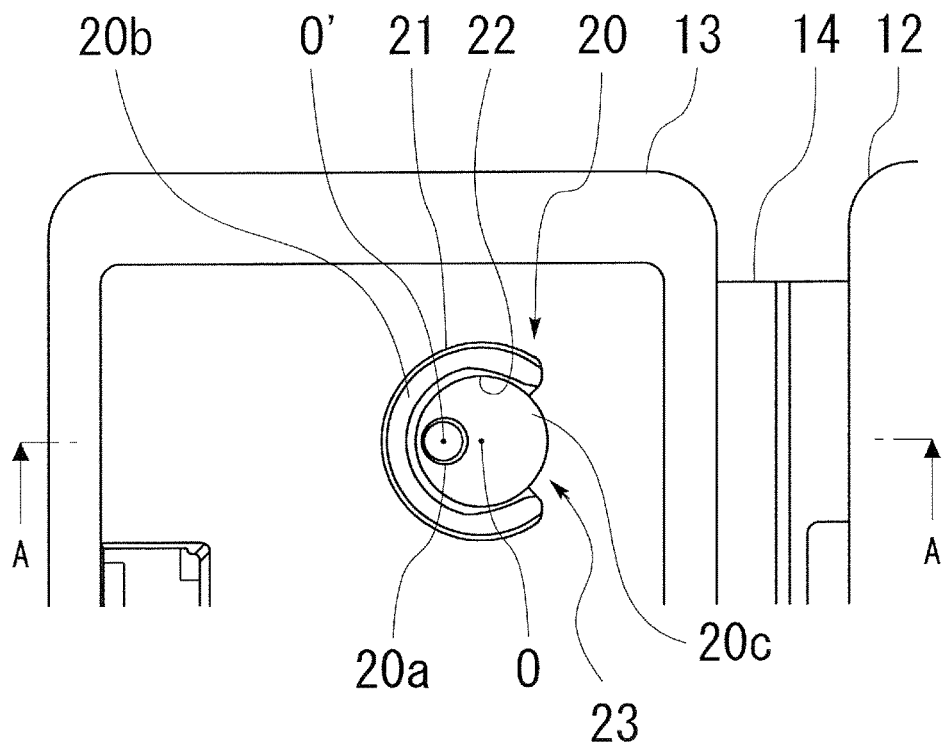
FIG. 8A is a plan diagram illustrating the schematic configuration of the insertion member for the needle of the syringe according to one embodiment.
Figure 8B:
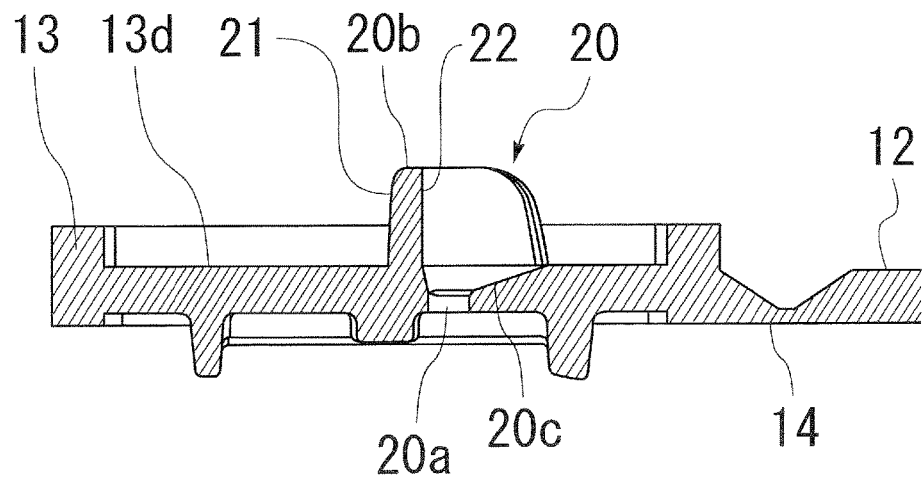
FIG. 8B is a cross-sectional diagram of the configuration illustrated in FIG. 8A.

In inserting the intraocular lens 2 into an eyeball using the insertion apparatus 1, firstly, an hyaluronic acid which is a lubricant for the intraocular lens 2 is injected into a position where the hyaluronic acid is necessary by inserting a needle of a syringe through the needle hole 20*a*. Here, the insertion member 20 of the present embodiment is described with reference to FIG. 8A and FIG. 8B. FIG. 8A is a top plan diagram of the insertion member 20, and FIG. 8B is a cross-sectional diagram of the insertion member 20 taken along a line A-A in FIG. 8A. In FIG. 8B, a cross sectional member is indicated by hatching. As illustrated in FIG. 8A, the guide wall member 20*b* of the insertion member 20 is configured such that an outer wall 21 and an inner wall 22 of the guide wall member 20*b* surround the needle hole 20*a* in an arcuate shape when the guide wall member 20*b* is viewed from above the stage lid member 13. At the time of inserting a needle of a syringe into the inside of the needle hole 20*a*, a user can grasp the position of the needle hole 20*a* by confirming the position of the guide wall member 20*b*. In this manner, the guide wall member 20*b* has an effect of enhancing visibility of the needle hole 20*a*.

As can be understood from FIG. 8A, the needle hole 20*a* is arranged at the position closer to the guide wall member 20*b* than an arcuate opening member 23 which the guide wall member 20*b* forms. Further, the center O of an arc which the inner wall 22 of the guide wall member 20*b* forms is offset from the center O' of the needle hole 20*a*. Accordingly, when the distal end of the needle of a syringe is brought into contact with the guide wall member 20*b*, a user can guide a distal end of a needle to an area in the vicinity of the needle hole 20*a* along the inner wall 22 of the guide wall member 20*b*. In the present embodiment, the guide wall member 20*b* has an arcuate shape when viewed from above the stage lid member 13. However, provided that the guide wall member 20*b* has a function of guiding a needle of a syringe to the needle hole 20*a*, the guide wall member may have any arbitrary shape and is configured such that the center (the center of gravity) of the guide wall member and the center of the needle hole 20*a* on the upper surface of the stage lid member 13 do not agree with each other.

In the present embodiment, the guide wall member 20*b* extends substantially perpendicular to an upper surface 13*d* of the stage lid member 13. A thickness of the guide wall member 20*b* is suitably set such that a needle of a syringe to be used does not penetrate the guide wall member 20*b*. A height of the guide wall member 20*b* from the upper surface 13*d* is suitably set to an extent that a user can confirm the guide wall member 20*b* by his naked eyes. As one example, a thickness of the guide wall member 20*b* can be set to 0.5 mm, and a height of the guide wall member 20*b* from the upper surface 13*d* can be set to 1.5 mm. A diameter of an arc which the inner wall 22 forms can be set to 2.0 mm, for example.

As illustrated in FIG. 8B, the inclined member 20*c* has a funnel shape. The inclined member 20*c* is connected with the inner wall 22 of the guide wall member 20*b* at an upper end thereof, and is connected with an inner surface of the needle hole 20*a* at a lower end thereof. In the present embodiment, the inclined member 20*c* is formed on the insertion hole 20. Accordingly, a user can guide a distal end of a needle to the needle hole 20*a* from the inclined member 20*c* by enabling sliding of the distal end of the needle not only in the case where a distal end of a needle of a syringe is brought into contact with the inner wall 22 but also in the case where the distal end of the needle of the syringe is brought into contact with the inclined member 20*c*.

Figure 9:
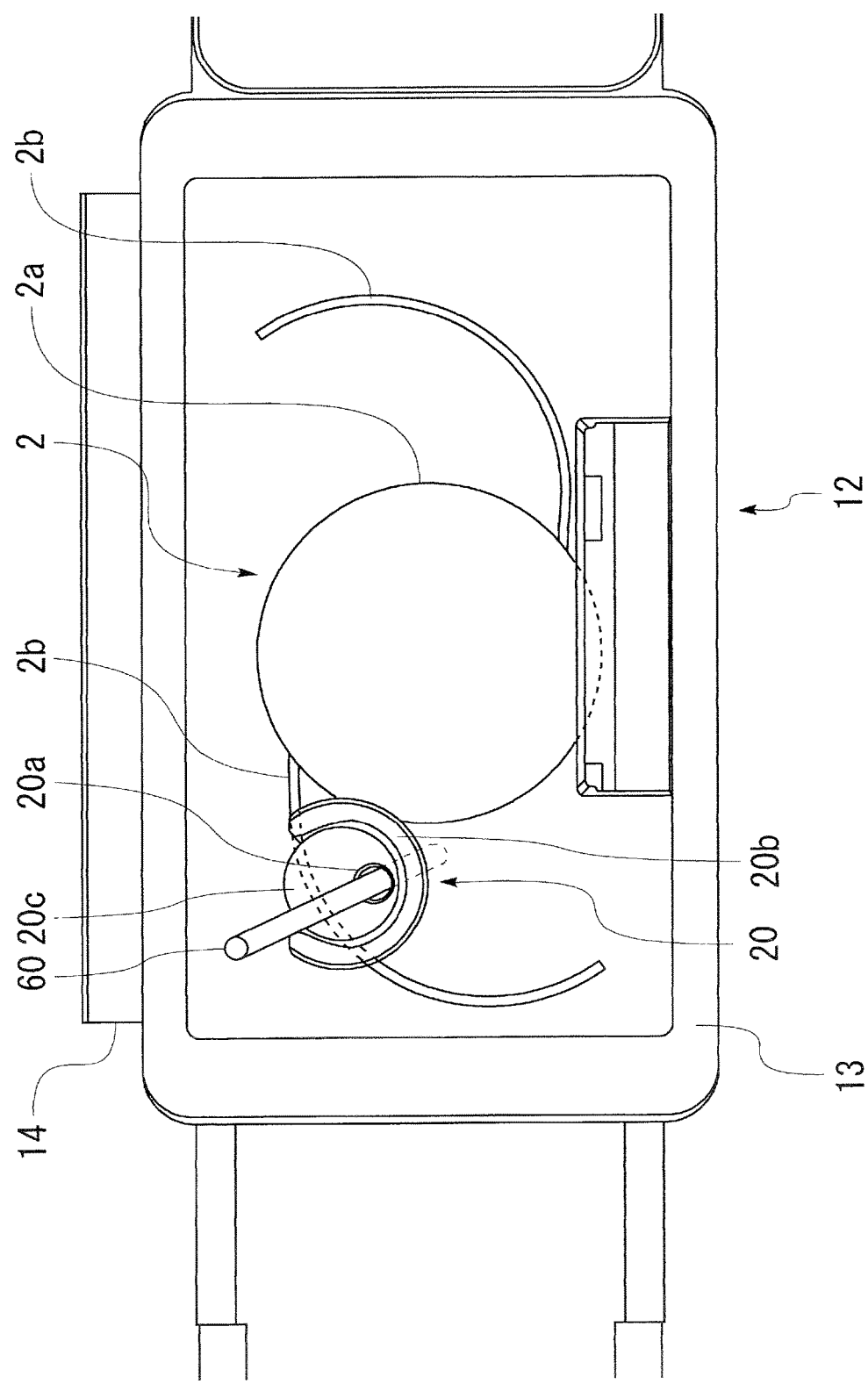
FIG. 9 is a diagram illustrating the schematic positional relationship between the needle of the syringe, a needle hole, and the intraocular lens according to one embodiment.

FIG. 9 illustrates one example of the positional relationship between the intraocular lens 2, the insertion member 20 and a needle 60 of a syringe when the needle 60 is inserted into the stage member 12 through the needle hole 20*a* after the intraocular lens 2 is set on the stage member 12 and the stage lid member 13 is closed. FIG. 9 illustrates a state where the needle 60 of the syringe is brought into contact with the guide wall member 20*b*. For the sake of convenience, in FIG. 9, a portion of the intraocular lens 2 is indicated by a solid line. However, the intraocular lens 2 is accommodated in the accommodating member formed of the stage member 12 and the stage lid member 13. When the needle 60 of the syringe is made to pass through the needle hole 20*a*, the movement of the needle 60 in a horizontal direction (a direction horizontal to the upper surface 13*d* of the stage lid member 13) is restricted by the needle hole 20*a* and the guide wall member 20*b*. Accordingly, an inclination angle of the needle 60 of the syringe with respect to a direction perpendicular to the upper surface 13*d* of the stage lid member 13 (a direction toward a viewer's side with respect to a paper surface on which FIG. 9 is drawn) is restricted to a value which falls within a predetermined range by the guide wall member 20b. The predetermined range within which the inclination angle is restricted is determined based on a height of the guide wall member 20b, a relative position between the guide wall member 20b and the needle hole 20a, a diameter of the needle hole 20a and the like.

By restricting the movement of the needle 60 of the syringe as described above, it is possible to prevent a distal end of the needle 60 of the syringe from being brought into contact with the lens body 2a of the intraocular lens 2 positioned on the stage member 12. Further, in the present embodiment, the guide wall member 20b is configured such that the guide wall member 20b is formed into an arcuate shape as viewed from above the stage lid member 13 so that the guide wall member 20b does not completely surround the needle hole 20a and has the opening member 23. With such a configuration, the needle 60 of the syringe can be easily guided to the needle hole 20a. Further, a portion of the guide wall member 20b is opened and hence, after the needle 60 of the syringe is inserted into the needle hole 20a, the movement of the needle 60 of the syringe is not restricted by the guide wall member 20b at the opening member 23. Accordingly, the movement of the needle 60 of the syringe is allowed to an extent that the needle 60 is not brought into contact with the lens body 2a of the intraocular lens 2, and hence, the degree of freedom in movement of the needle 60 of the syringe can be also enhanced.

In the present embodiment, with an aim to facilitate the guiding of the needle 60 of the syringe into the needle hole 20a after the stage lid member 13 is closed, the opening member 23 of the guide wall member 20b is formed on the upper surface 13d of the stage lid member 13 in a direction perpendicular to the fore-and-aft direction (longitudinal direction) of the nozzle body 10. With such a configuration, handling of the insertion apparatus 1 can be enhanced while properly restricting the position of the needle 60 of the syringe. Provided that the needle 60 of the syringe is not brought into contact with the lens body 2a of the intraocular lens, the position where the opening member 23 is formed can be suitably changed.

A user inserts the needle 60 of the syringe through the needle hole 20a and injects a hyaluronic acid into the stage member 12 and, thereafter, the user removes the positioning member 50 from the nozzle body 10. With such an operation, the first placing members 54, 54 and the second placing members 56, 56 which support the lens body 2a of the intraocular lens 2 are retracted from the setting surface 12b, and the intraocular lens 2 is placed on the setting surface 12b in a movable manner.

Subsequently, the distal end member 10a of the nozzle member 15 of the nozzle body 10 is inserted into an incision formed in an ophthalmic tissue. In this stage of operation, the distal end member 10a has an oblique opening shape and hence, the insertion of the distal end member 10a into the incision can be easily performed. Then, the nozzle member 15 is inserted into the incision and, thereafter, the pushing plate member 33 of the plunger 30 is pushed toward a distal end side of the nozzle body 10 in such a state. With such an operation, a distal end of the operating member 31 of the plunger 30 is brought into contact with the outer periphery of the lens body 2a of the intraocular lens 2 which is set on the setting surface 12b, and the intraocular lens 2 is guided toward the distal end member 10a by the plunger 30, and is released into the inside of an eyeball through the opening of the distal end member 10a.

Although the present embodiment is described as above, the configurations and the processes of the information processing apparatus are not limited to those as described above and various variations may be made to the embodiment described herein within the technical scope of the above embodiment. For example, in the above-mentioned description, the guide wall member 20b of the insertion member 20 is formed into an arcuate shape when the guide wall member 20b is viewed from above the stage lid member 13. However, provided that a user can visually recognize the guide wall member 20b and the position of the needle hole 20a, a shape of the guide wall member 20b is not limited to the above-mentioned shape and can be suitably changed. Also in the description of the following modifications made hereinafter, the shapes of respective guide wall members can be suitably changed.

Six modifications of the above-mentioned embodiment are exemplified hereinafter. In the description made hereinafter, respective constitutional elements corresponding to the constitutional elements of the above-mentioned embodiment are given the same symbols, and the repeated description of the constitutional elements is omitted unless otherwise specified.

[Modification 1]

Figure 10:
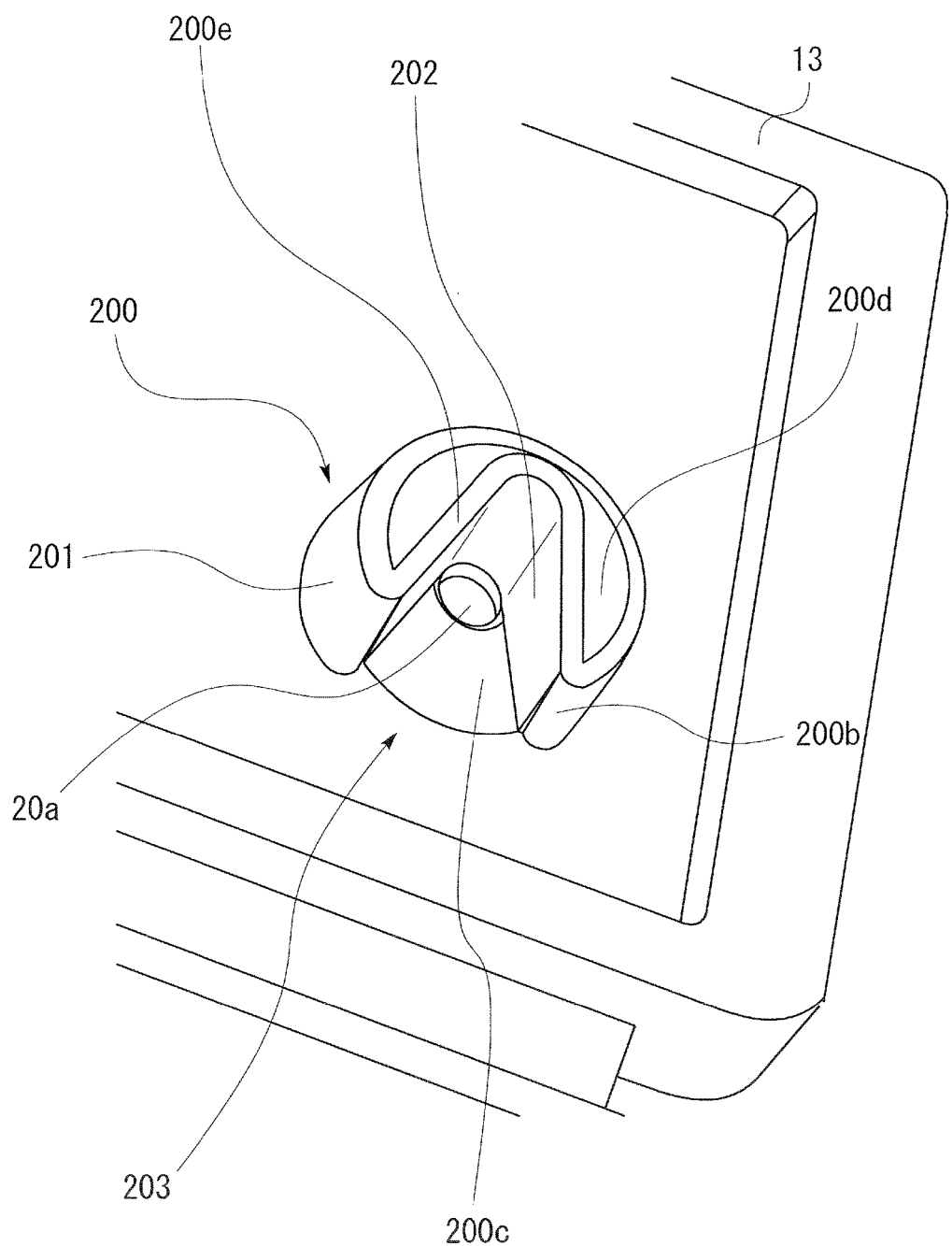
FIG. 10 is a diagram illustrating the schematic configuration of an insertion member for a needle of a syringe according to a modification 1.

FIG. 10 is a perspective diagram illustrating the schematic configuration of an insertion member 200 according to a modification 1. As illustrated in FIG. 10, the insertion member 200 has a needle hole 20a, a guide wall member 200b, and an inclined member 200c. A shape of an outer wall 201 of the guide wall member 200b as viewed from above a stage lid member 13 is equal to the shape of the outer wall of the guide wall member 200b in the above-mentioned embodiment, and an opening member 203 which corresponds to the opening member 23 of the above-mentioned embodiment is formed on the guide wall member 200b. The needle hole 20a is formed in an upper surface of the stage lid member 13 at the position closer to an inner wall 202 of the guide wall member 200b than the opening member 203. The inner wall 202 of the guide wall member 200b is formed in an approximately V shape as viewed from above the stage lid member 13. Further, the inclined member 200c is equal to the inclined member 20c of the above-mentioned embodiment except for that the inclined member 200c is formed into an arcuate shape defined by the inner wall 202 and the needle hole 20a.

As illustrated in FIG. 10, even when the guide wall member 200b is disposed adjacent to the needle hole 20a, a user can use the guide wall member 200b of the insertion member 200 as an index indicating the position of the needle hole 20a. In the same manner as the above-mentioned embodiment, the guide wall member 200b and the inclined member 200c play a role of guiding a needle of a syringe to the needle hole 20a. Further, after a needle of a syringe is inserted into the needle hole 20a, the movement of the needle is restricted by the guide wall member 200b such that the needle is not brought into contact with the lens body 2a of the intraocular lens 2.

[Modification 2]

Figure 11:
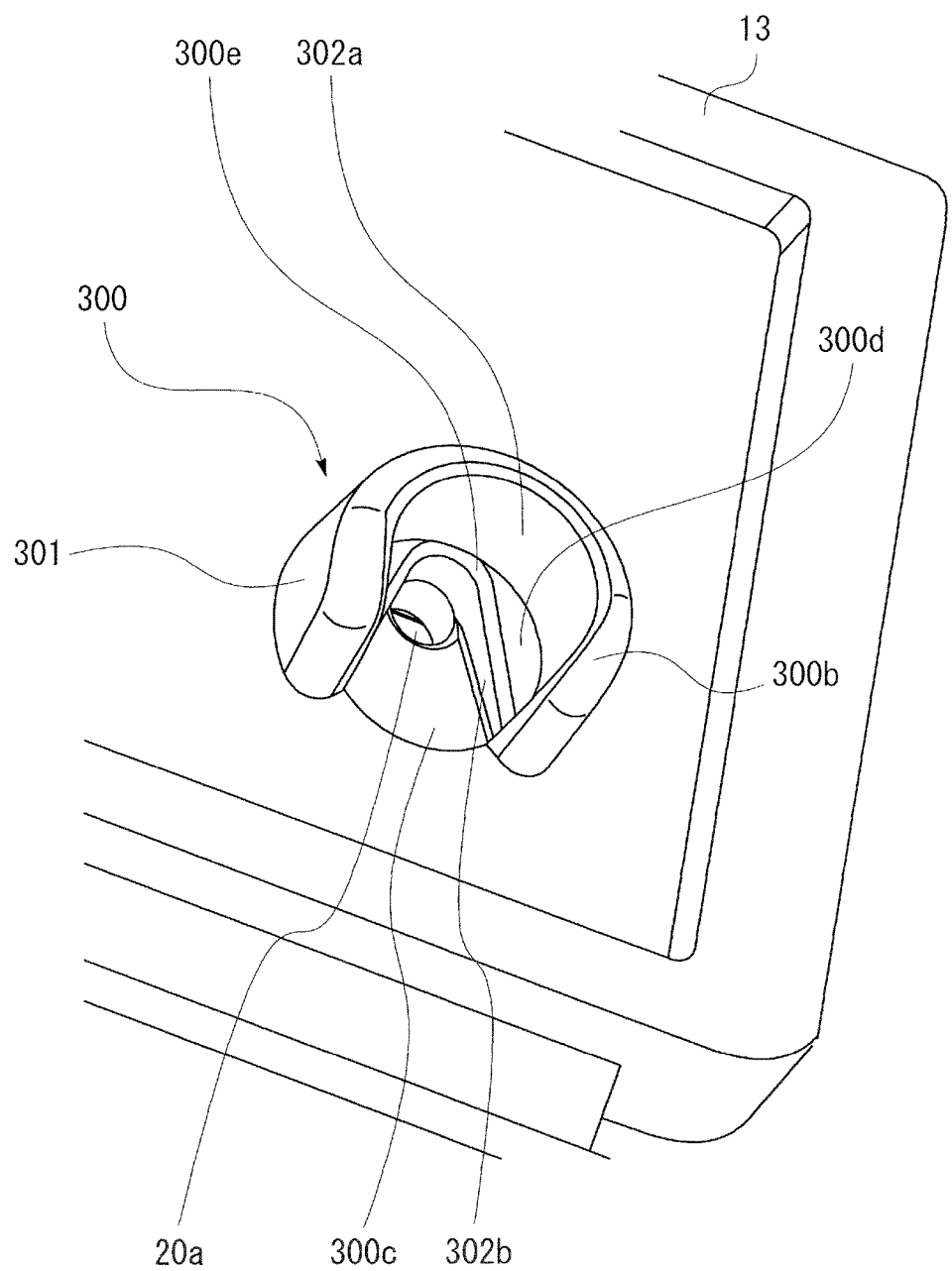
FIG. 11 is a diagram illustrating the schematic configuration of an insertion member for a needle of a syringe according to a modification 2.

FIG. 11 is a perspective diagram illustrating the schematic configuration of an insertion member 300 according to a modification 2. In the modification 2, a height of the guide wall member 200b on an inner wall 202 side in a thickness direction in the modification 1 is set lower than a height of the guide wall member 200b on an outer wall 201 side. Accordingly, as illustrated in FIG. 11, in addition to a first inner wall 302a, a stepped member formed of an upper surface 300d, an R member 300e and a second inner wall 302b is formed on a guide wall member 300b. An inclined member 300c and an opening member 303 respectively correspond to the inclined member 200c and the opening member 203 in the modification 1.

Also in the modification 2, a user can use the guide wall member 300b of the insertion member 300 as an index indicating the position of a needle hole 20a. Further, after a needle of a syringe is inserted into the needle hole 20a, the movement of the needle is restricted by the guide wall member 300b such that the needle is not brought into contact with the lens body 2a of the intraocular lens 2.

As illustrated in FIG. 11, the second inner wall 302b which is a stepped member formed on the guide wall member 300b also plays a role of guiding a needle of a syringe to the needle hole 20a. Further, the movement of the needle of the syringe inserted into the needle hole 20a is restricted also by the stepped member. In the modification 2, by providing the stepped member such that a height of a member of an inner wall is set lower than a height of an outer wall as described above, a wall thickness of the member can be reduced in so-called injection molding. With such a configuration, compared to the case where the guide wall member is formed with a height of the second inner wall 302b set equal to a height of the outer wall 301, that is, compared to the case where the guide wall member 200b described in the modification 1 is used as the guide wall member, the modification 2 can also acquire an effect of preventing occurrence of shrinkage at the time of forming the insertion member by injection molding.

[Modification 3]

Figure 12A:
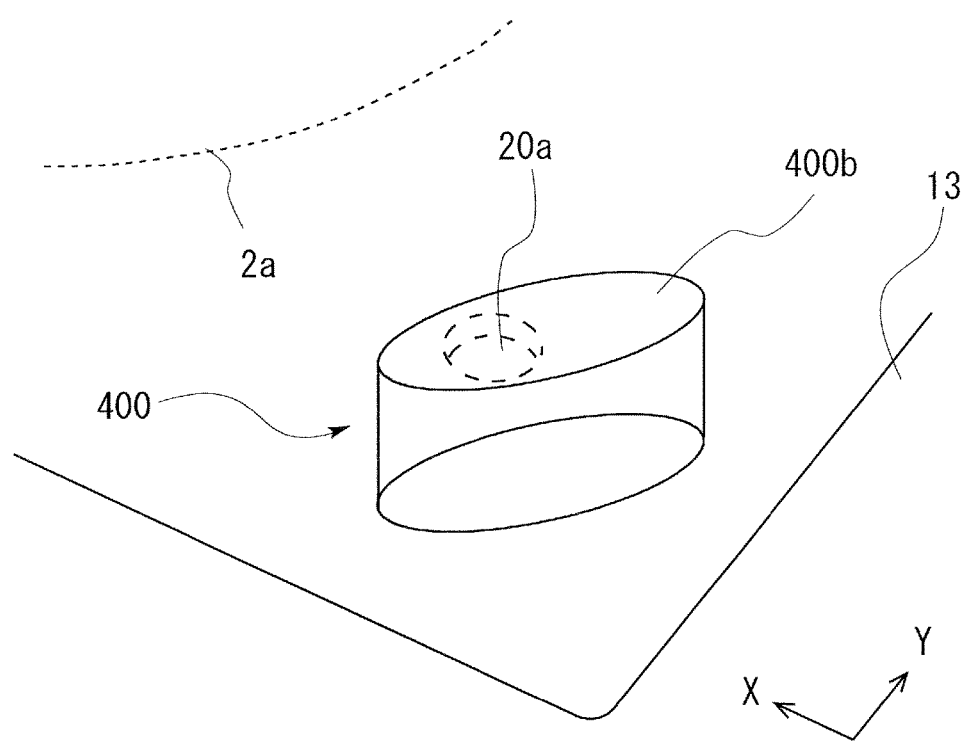
FIG. 12A and FIG. 12B is a diagram illustrating the schematic configuration of an insertion member for a needle of a syringe according to a modification 3.
Figure 12B:
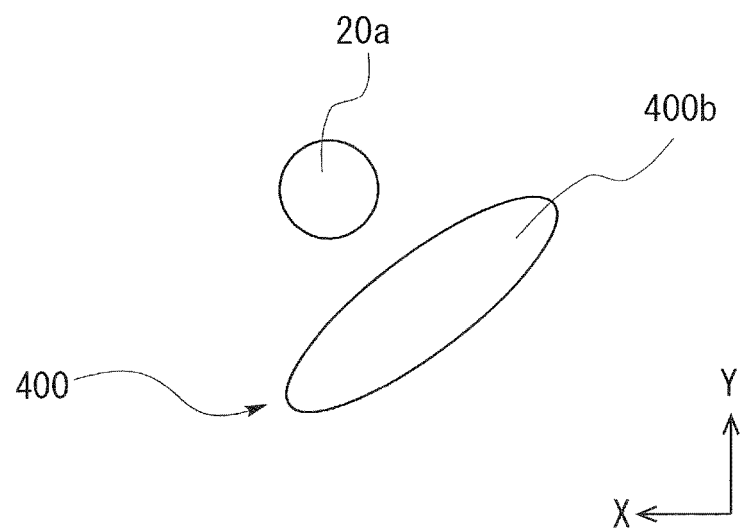

FIG. 12A and FIG. 12B are diagrams illustrating the schematic configuration of an insertion member 400 according to a modification 3. In the description made hereinafter, as illustrated in the respective drawings, an X axis and a Y axis which are orthogonal to each other are set on a plane parallel to an upper surface of a stage lid member 13. FIG. 12A is a perspective diagram, and FIG. 12B is a plan diagram. As illustrated in FIG. 12A and FIG. 12B, a guide wall member 400b is a flat-plate-shaped wall formed at a position adjacent to a needle hole 20a. The position of the guide wall member 400b and the like may be suitably set corresponding to the positional relationship between the needle hole 20a and a lens body 2a of a positioned intraocular lens. Also in the modification 3, a user can use the guide wall member 400b as an index indicating the position of the needle hole 20a. Further, when a needle of a syringe is inserted into the needle hole 20a, the movement of the needle of the syringe is restricted by the guide wall member 400b such that the needle of the syringe is not brought into contact with the lens body 2a.

[Modification 4]

Figure 13A:
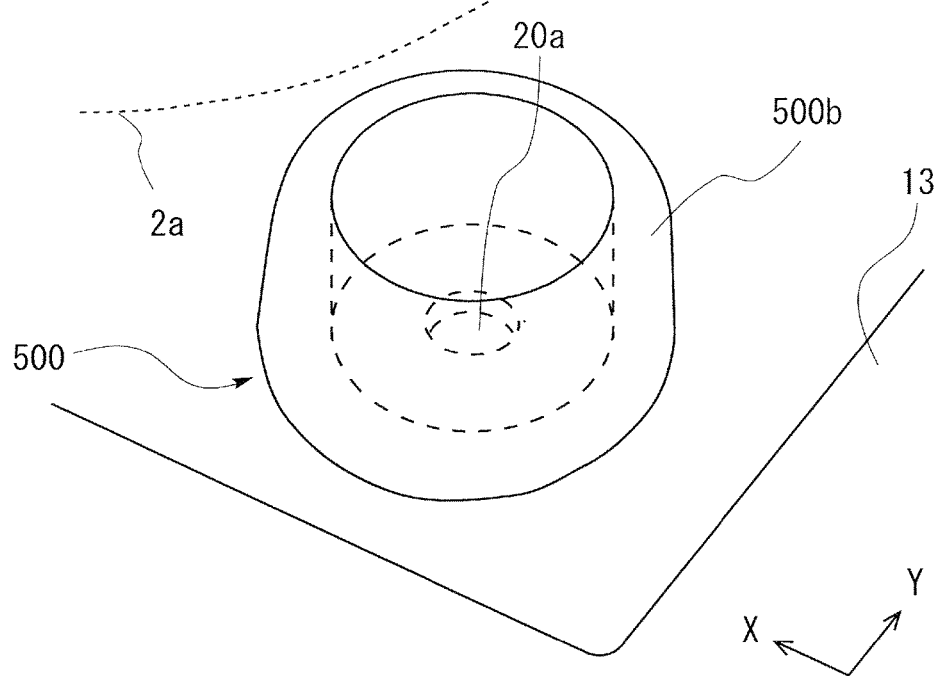
FIG. 13A and FIG. 13B is a diagram illustrating the schematic configuration of an insertion member for a needle of a syringe according to a modification 4.
Figure 13B:
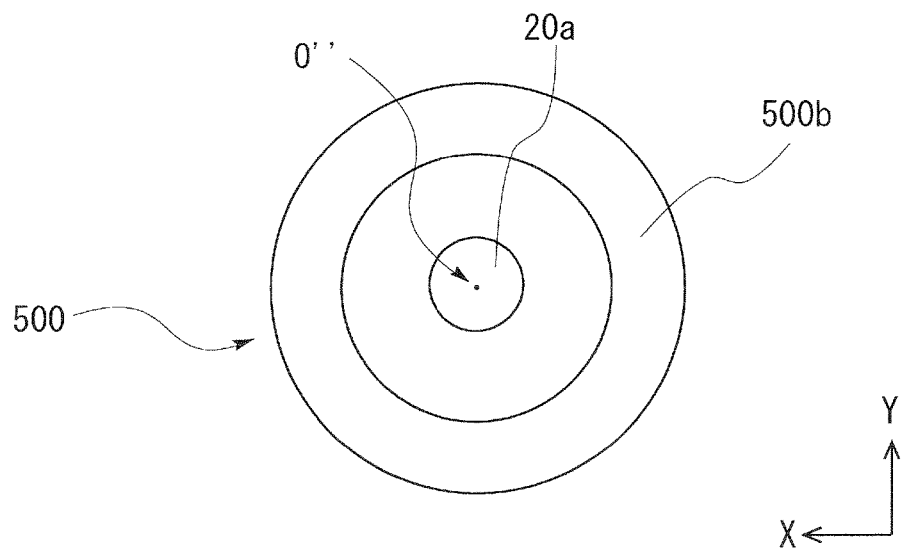

FIG. 13A and FIG. 13B are diagrams illustrating the schematic configuration of an insertion member 500 according to a modification 4. FIG. 13A is a perspective diagram, and FIG. 13B is a plan diagram. As illustrated in FIG. 13A and FIG. 13B, a guide wall member 500b is formed in a region which annularly surrounds the periphery of a needle hole 20a. As illustrated in FIG. 13B which is a plan diagram, the needle hole 20a and an outer wall and an inner wall of the guide wall member 500b are configured to be arranged concentrically (the center O"). Also in the modification 4, a user can use the guide wall member 500b as an index indicating the position of the needle hole 20a. Further, when a needle of a syringe is inserted into the needle hole 20a, the movement of the needle of the syringe is restricted by the guide wall member 500b such that the needle of the syringe is not brought into contact with the lens body 2a.

[Modification 5]

Figure 14A:
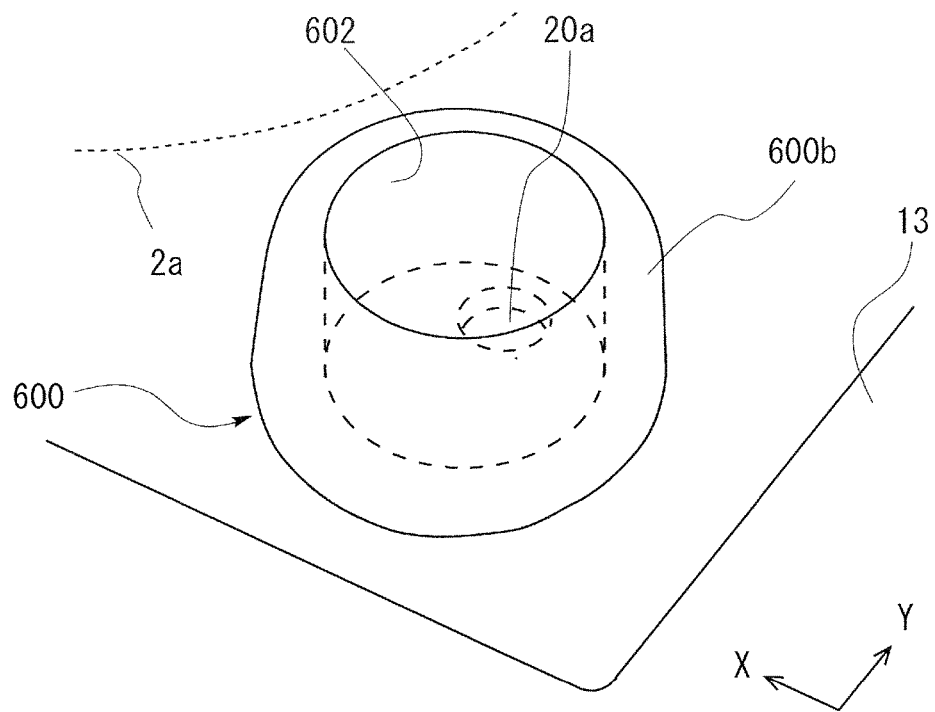
FIG. 14A and FIG. 14B is a diagram illustrating the schematic configuration of an insertion member for a needle of a syringe according to a modification 5; and FIG. 15A
Figure 14B:
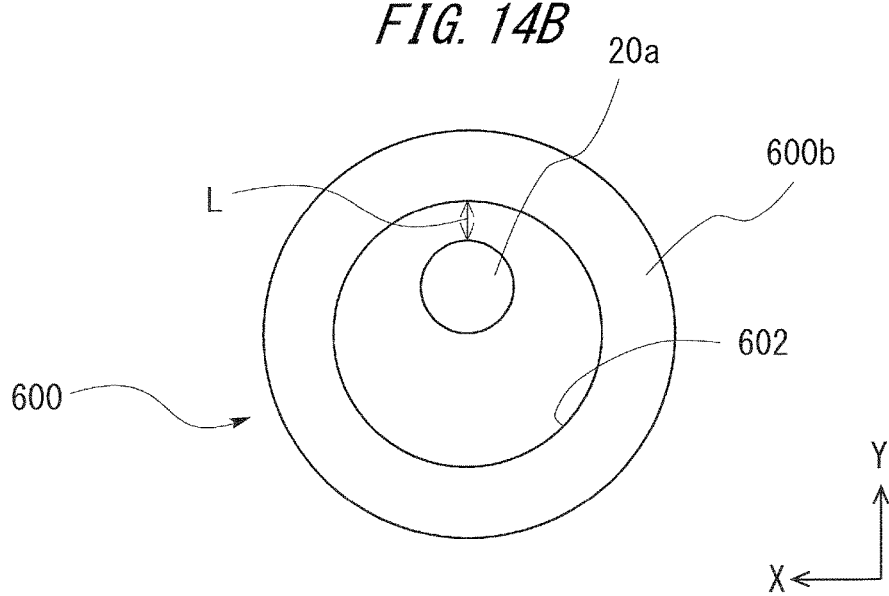

FIG. 14A and FIG. 14B are diagrams illustrating the schematic configuration of an insertion member 600 according to a modification 5. FIG. 14A is a perspective diagram, and FIG. 14B is a plan diagram. The insertion member 600 in the modification 5 has substantially the same configuration as the insertion member 500 except for that the center of the insertion member 500 in the modification 4 is offset from the center of the needle hole 20a. That is, in the modification 5, as viewed in a plan diagram, the needle hole 20a is configured such that a distance L between the needle hole 20a and a predetermined portion of an inner wall 602 of a guide wall member 600b is set shorter than a distance between the needle hole 20a and other portions of the inner wall 602. Here, "predetermined portion" is determined by taking into account the easiness of guiding a needle of a syringe to the needle hole 20a and the proper restriction of the movement of a needle of a syringe so as to prevent the needle of the syringe from being brought into contact with the lens body 2a and the like. Also in the modification 5, a user can use the guide wall member 600b as an index indicating the position of the needle hole 20a. Further, when a needle of a syringe is inserted into the needle hole 20a, the movement of the needle of the syringe is restricted by the guide wall member 600b such that the needle of the syringe is not brought into contact with the lens body 2a.

[Modification 6]

Figure 15A:
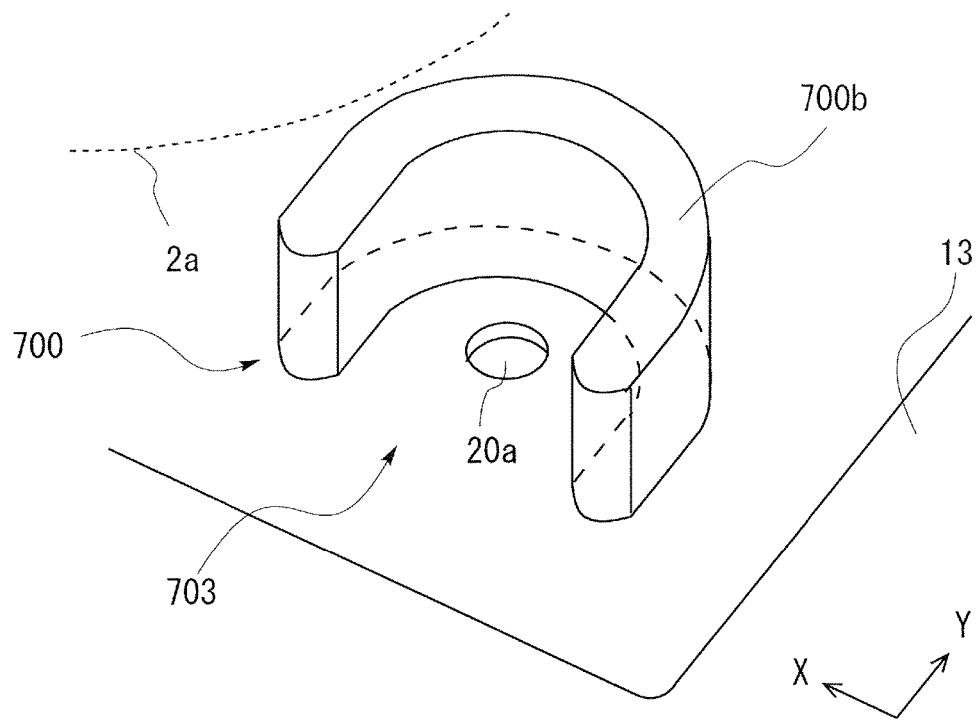
FIG. 15B is a diagram illustrating the schematic configuration of an insertion member for a needle of a syringe according to a modification 6.
Figure 15B:
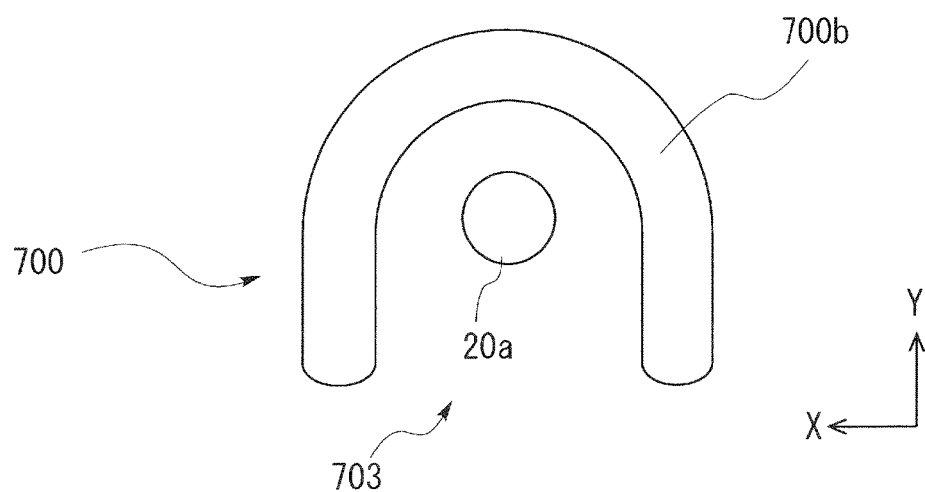

FIG. 15A and FIG. 15B are diagrams illustrating the schematic configuration of an insertion member 700 according to a modification 6. FIG. 15A is a perspective diagram, and FIG. 15B is a plan diagram. As viewed in a plan diagram, an approximately U-shaped guide wall member 700b having an opening member 703 is formed in the insertion member 700 of the modification 6. The guide wall member 700b is arranged so as to surround a needle hole 20a. The position of the guide wall member 700b and the position of the opening member 703 with respect to a position of the needle hole 20a are determined by taking into account the easiness of guiding a needle of a syringe to the needle hole 20a and the proper restriction of the movement of the needle of the syringe so as to prevent the needle of the syringe from coming into contact with the lens body 2a and the like. Also in the modification 6, a user can use the guide wall member 700b as an index indicating the position of the needle hole 20a. Further, by forming the opening member 703, compared to cases described in the modifications 4, 5 where the opening member 703 is not formed, the user can more easily guide the needle of the syringe to the needle hole 20a. Further, when the needle of the syringe is inserted into the needle hole 20a, the movement of the needle of the syringe is restricted by the guide wall member 700b such that the needle of the syringe is not brought into contact with the lens body 2a. Also in the above-mentioned modifications 3 to 6, an inclined member substantially equal to the inclined members 20c, 200c, 300c can be formed between the guide wall member and the needle hole 20a.

[REFERENCE SIGNS LIST]

1 insertion apparatus
2 intraocular lens
2a lens body
2b support member
10 nozzle body
10a distal end member of nozzle body
10b rear end member of nozzle body
12 stage member 13 stage lid member
20, 200, 300, 400, 500, 600, 700 insertion member
20a needle hole
20b, 200b, 300b, 400b, 500b, 600b, 700b guide wall member
20c, 200c, 300c inclined member
21, 201, 301 outer wall
22, 202, 602 inner wall
302a first inner wall
302b second inner wall
23, 203, 303, 603, 703 opening member
30 plunger
50 positioning member
60 needle of syringe

What is claimed is:

1. An intraocular lens insertion apparatus comprising:
an accommodating member integrally or independently formed on an apparatus body which is inserted into an eyeball, allowing arrangement of the intraocular lens in the apparatus body by accommodating the intraocular lens therein, and having a hole through which a needle of a syringe which supplies a lubricant to the intraocular lens passes; and
a guide wall member formed on the accommodating member at a position adjacent to the hole, and being configured to guide the needle of the syringe to the hole,
wherein the guide wall member is positioned in an area surrounding the hole, and wherein the guide wall member does not completely surround a periphery of the hole such that the guide wall member is positioned around a part of the periphery of the hole, and
wherein a diameter of the guide wall member is larger than a diameter of the hole.

2. The intraocular lens insertion apparatus according to claim 1, wherein the guide wall member is configured so as to prevent the needle of the syringe from coming into contact with a lens body of the intraocular lens accommodated in the accommodating member in a state where the needle of the syringe which is made to pass through the hole is brought into contact with the guide wall.

3. The intraocular lens insertion apparatus according to claim 2, wherein a distance from the center of the hole to a predetermined portion of an inner wall of the guide wall member is shorter than a distance from the center of the hole to another portion of the inner wall of the guide wall member.

4. The intraocular lens insertion apparatus according to claim 2, wherein a distance from the center of the hole to a predetermined portion of an inner wall of the guide wall member is shorter than a distance from the center of the hole to another portion of the inner wall of the guide wall member.

5. The intraocular lens insertion apparatus according to claim 4, wherein the guide wall member has an opening member which allows movement of the needle of the syringe within a range where the needle of the syringe which is made to pass through the hole is not brought into contact with a lens body of the intraocular lens accommodated in the accommodating member.

6. The intraocular lens insertion apparatus according to claim 2, wherein the guide wall member has an opening member which allows movement of the needle of the syringe within a range where the needle of the syringe which is made to pass through the hole is not brought into contact with a lens body of the intraocular lens accommodated in the accommodating member.

7. The intraocular lens insertion apparatus according to claim 1, wherein a distance from the center of the hole to a predetermined portion of an inner wall of the guide wall member is shorter than a distance from the center of the hole to another portion of the inner wall of the guide wall member.

8. The intraocular lens insertion apparatus according to claim 7, wherein the guide wall member has an opening member which allows movement of the needle of the syringe within a range where the needle of the syringe which is made to pass through the hole is not brought into contact with a lens body of the intraocular lens accommodated in the accommodating member.

9. The intraocular lens insertion apparatus according to claim 1, wherein an inclined member which connects an inner wall of the guide wall member and the hole is formed on the guide wall member.

10. The intraocular lens insertion apparatus according to claim 1, wherein a stepped member is formed on the guide wall member by setting a height of an inner wall side of the guide wall member in a thickness direction lower than a height of an outer wall of the guide wall member.

11. The intraocular lens insertion apparatus according to claim 10, wherein the guide wall member has an opening member which allows movement of the needle of the syringe within a range where the needle of the syringe which is made to pass through the hole is not brought into contact with a lens body of the intraocular lens accommodated in the accommodating member.

12. The intraocular lens insertion apparatus according to claim 1, wherein the hole is formed on a distal end side of the apparatus body with respect to the intraocular lens accommodated in the accommodating member.

13. The intraocular lens insertion apparatus according to claim 1, wherein the accommodating member is integrally formed on the apparatus body.

14. The intraocular lens insertion apparatus according to claim 1, wherein a height of the guide wall member formed on the accommodating member is higher than a surface of the accommodating member.

15. The intraocular lens insertion apparatus according to claim 1, wherein the guide wall member has an inner wall and an outer wall, and wherein a height of the inner wall is lower than a height of the outer wall.

16. An intraocular lens insertion apparatus comprising:
an accommodating member integrally or independently formed on an apparatus body which is inserted into an eyeball, allowing arrangement of the intraocular lens in the apparatus body by accommodating the intraocular lens therein, and having a hole through which a needle of a syringe which supplies a lubricant to the intraocular lens passes; and
a guide wall member formed on the accommodating member at a position adjacent to the hole, and being configured to guide the needle of the syringe to the hole,
wherein the guide wall member is positioned in an area surrounding the hole, and wherein the guide wall member does not completely surround a periphery of the hole such that the guide wall member is positioned around a part of the periphery of the hole,
the intraocular lens is accommodated in the accommodating member before the insertion apparatus is placed on a market, and
wherein a diameter of the guide wall member is larger than a diameter of the hole.

17. An intraocular lens insertion apparatus comprising:
an accommodating member integrally or independently formed on an apparatus body which is inserted into an eyeball, allowing arrangement of the intraocular lens in the apparatus body by accommodating the intraocular lens therein, and having a hole through which a needle of a syringe which supplies a lubricant to the intraocular lens passes; and
a guide wall member formed on the accommodating member at a position adjacent to the hole, and being configured to guide the needle of the syringe to the hole,
wherein an inclined member which connects an inner wall of the guide wall member and the hole is formed,
the guide wall member is configured to project toward the outside of the accommodating member, and
the inclined member is configured to guide the needle of the syringe to the hole,
wherein a diameter of the guide wall member is larger than a diameter of the hole.

* * * * *